United States Patent [19]

Crowson

[11] Patent Number: 4,890,335
[45] Date of Patent: Jan. 2, 1990

[54] VENTILATED WELDING SHIELD

[76] Inventor: Arnold E. Crowson, Box 40 West Rte., Northome, Minn. 56661

[21] Appl. No.: 224,745

[22] Filed: Jul. 27, 1988

[51] Int. Cl.$^4$ .............................................. A61F 9/06
[52] U.S. Cl. ............................................ 2/8; 2/171.3; 219/147
[58] Field of Search .................... 2/8, 427, 436, 171.3; 219/147

[56] References Cited

U.S. PATENT DOCUMENTS

| | | | |
|---|---|---|---|
| 2,882,894 | 4/1959 | Fahey et al. | 2/8 X |
| 3,238,535 | 3/1966 | Richey | 2/8 |
| 3,467,965 | 9/1969 | Murphy | 2/8 |
| 3,649,964 | 3/1972 | Schoelz et al. | 2/171.3 X |
| 3,657,740 | 4/1972 | Cialone | 2/171.3 X |
| 4,293,757 | 10/1981 | Niemi | 2/8 X |
| 4,694,141 | 9/1987 | Hahn | 2/8 X |

FOREIGN PATENT DOCUMENTS

| | | | |
|---|---|---|---|
| 2409198 | 9/1975 | Fed. Rep. of Germany | 2/8 |
| 0563153 | 6/1975 | Switzerland | 2/8 |

Primary Examiner—Peter Nerbun
Attorney, Agent, or Firm—Leon Gilden

[57] ABSTRACT

A welding shield is designed to have a flow of ventilating air directed across both exterior and interior surfaces of a viewing lens forming a part of the shield. Both integral and separable air supply arrangements are used, and all of the supplied air is filtered before delivery across the shield.

1 Claim, 2 Drawing Sheets

VENTILATED WELDING SHIELD

BACKGROUND OF THE INVENTION

1. Field of the Invention

The present invention relates to welding equipment, and more particularly pertains to a new and improved welding shield which is provided with ventilation means.

2. Description of the Prior Art

The use of various ventilation devices for welding shields is well known in the prior art. All of these devices are directed to providing a flow of air around a welding hood or shield, and the prior art is replete with patented devices that accomplish the desired function.

A number of these prior art devices are directed to the providing of a tubular member around a welder's head, with such tubular member having a plurality of apertures through which a flow of ventilating air is directed. For example, U.S. Pat. Nos. 3,921,223 which issued to D. Hoyecki on Nov. 25, 1975 and 4,195,363 which issued to B. Jenson on Apr. 1, 1980 both disclose these type of devices. While being operable to provide a desired flow of ventilating air and to keep fumes and other noxious gasses away from the welder's face, it can be appreciated that neither of these devices are particularly adapted to maintain a clear viewing shield.

There are, however, patented ventilation devices which do provide for a flow of air over a viewing shield. For example, U.S. Pat. No. 3,922,722, which issued to Pokhodnya et al on Dec. 2, 1975, discloses the positioning of a perforated pipe on the outside of a helmet just under the light filtering viewing lens. A flow of air is directed to the pipe from an attached conduit, and the air passing outwardly through the perforations in the pipe passes over the viewing lens so as to keep an exterior surface thereof free from accumulated dust and other debris. At the same time, a flow of fresh air in front of the helmet reduces the amount of noxious fumes inhaled by the welder. While being operable to perform its intended function, it can be appreciated that condensation from the welder's breath will still condense on an interior surface of the viewing lens which could then result in substantial visibility problems.

By the same token, U.S. Pat. No. 4,309,774, which issued to C. Guzowski on Jan. 12, 1982, discloses a ventilated helmet wherein an electrically operated fan is adapted to move air to an interior portion thereof. The fan is operated through the use of a light sensitive, electrical energy producing cell, and the flow of air is designed to prevent the accumulation of gaseous fumes within the helmet during a welding operation. The invention disclosed in this patent is not designed to provide for a flow of air across an exterior surface of the viewing lens, nor is the air flow within the shield directed in a manner which would allow it to pass across the viewing lens so as to prevent condensation from forming thereon.

While all of these prior art devices are substantially similar in design and function, there would appear to be a continuing need for minor improvements which are of a patentable nature due to the crowded status of the art. Inasmuch as no single prior art patent discloses a means of providing ventilating air which would also keep a viewing lens free of dust accumulation and condensation, there would appear to be a continuing need for ventilation designs which would perform this desired function. In this respect, the present invention addresses this need.

SUMMARY OF THE INVENTION

In view of the foregoing disadvantages inherent in the known types of ventilated welding shields now present in the prior art, the present invention provides an improved ventilated welding shield construction wherein filtered air is delivered to a welder for breathing, while such flow of air is also directed across both exterior and interior surfaces of the viewing lens to maintain the same in a condition which is free of dust accumulation and condensation. As such, the general purpose of the present invention, which will be described subsequently in greater detail, is to provide a new and improved ventilated welding helmet construction which has all the advantages of the prior art ventilated welding helmets and none of the disadvantages.

To attain this, the present invention is directed to the use of a separable or integral manifold attached proximate the viewing lens of a helmet. Either a connection hose or a direct blower attachment can be made to the manifold, and power for operating the blower can be supplied by a battery pack or an external alternating current power supply. The incoming air to the blower is filtered prior to passing therethrough, and the manifold includes appropriately positioned air directing slits which provide an even flow of air over both exterior and interior surfaces of the lens. The air directing slits are designed to permit a larger flow of air across a mid section of a viewing lens so that the air stream is directed outwardly to completely cover a lens after striking the intermediate portion thereof. In this regard, each air directing slit is concavely shaped so as to allow a larger flow of air from a mid portion thereof.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto. Those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new and improved welding helmet ventilation device which has all the advantages of the prior art welding helmet ventilation devices and none of the disadvantages.

It is another object of the present invention to provide a new and improved welding helmet ventilation device which may be easily and efficiently manufactured and marketed.

It is a further object of the present invention to provide a new and improved welding helmet ventilation device which is of a durable and reliable construction.

An even further object of the present invention is to provide a new and improved welding helmet ventilation device which is susceptible of a low cost of manufacture with regard to both materials and labor, and which accordingly is then susceptible of low prices of sale to the consuming public, thereby making such welding helmet ventilation devices economically available to the buying public.

Still yet another object of the present invention is to provide a new and improved welding helmet ventilation device which provides in the apparatuses and methods of the prior art some of the advantages thereof, while simultaneously overcoming some of the disadvantages normally associated therewith.

Still another object of the present invention is to provide a new and improved welding helmet ventilation device which facilitates a flow of filtered air along both exterior and interior surfaces of a helmet viewing lens.

Yet another object of the present invention is to provide a new and improved welding helmet ventilating device which operates to prevent dust and condensation accumulation on both surfaces of a viewing lens.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENTS

Figure 1:
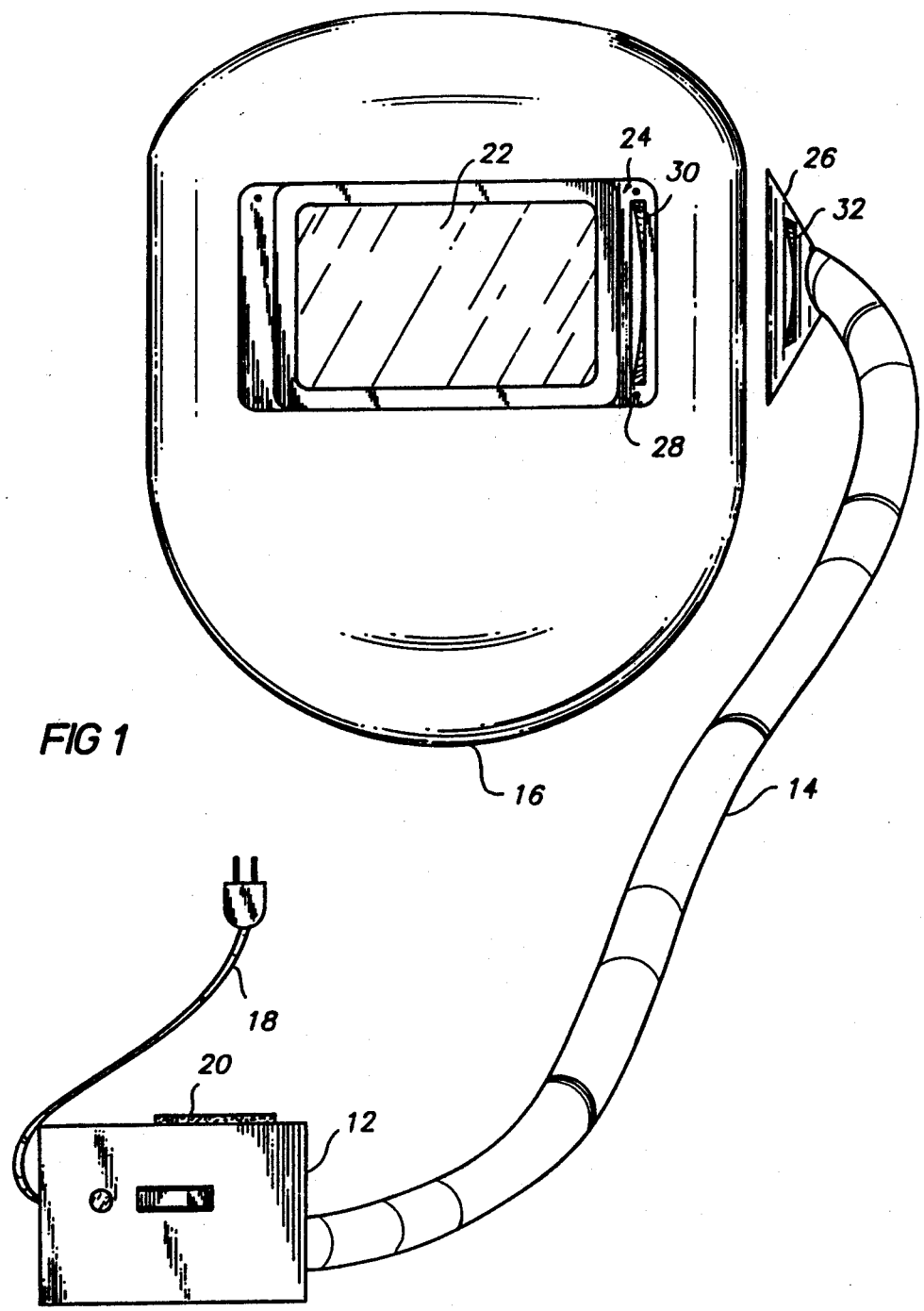
FIG. 1 is a front end elevation view of a first embodiment of a welding helmet ventilating device comprising the present invention.

With reference now to the drawings, and in particular to FIG. 1 thereof, a new and improved welding helmet ventilating device embodying the principles and concepts of the present invention and generally designated by the reference numeral 10 will be described.

More specifically, it will be noted that the welding helmet ventilating device 10 in a first embodiment thereof comprises a remotely positioned air blower unit 12 designed to deliver a flow of air through a conduit 14 to a welding face shield 16. As illustrated, power for operating the blower 12 may be from an external alternating current supply through the use of an electrical connector 18 or alternatively, a battery powered unit is within the intent and purview of the present invention.

The air intake of the blower 12 is covered with a charcoal filter 20 so as to cleanse the air before delivery through the conduit 14.

As clearly illustrated in the drawings, the welding face shield 16 includes an outwardly positioned conventional light filtering viewing lens 22. In this regard, the light filtering viewing lens 22 is operably mounted to an outwardly extending housing 24 which is fixedly secured to the body portion of the shield 16.

The air flow conduit 14 is provided with a nozzle member 26 that is attachable to a side portion 28 of the lens holding housing 24. The nozzle 26 may be attached to the lens holder 24 by any known conventional means, such as through the use of hook and loop fasteners, threaded members, and the like, and all such conceivable fastening means are within the intent of the claims appended hereto. Accordingly, no specific description of such fastening means is provided.

As further illustrated, the lens holding housing 24 is provided with a through-extending slot 30 over which the nozzle 26 is attached. The slot 30 facilitates an air flow across an interior surface of the lens 22 and is also designed in a concavely-shaped manner whereby a mid portion of the slot will facilitate a greater flow of air across the lens than will end portions of the slot. Further, the slot 30 is directed towards a mid interior portion of the lens 22 so that air delivered therethrough will strike the center of the lens and radiate outwardly therefrom. As such, a lesser flow of air is provided along top and bottom edges of the lens 22 due to the concave shape of the slot 30.

By the same token, recognizing that it is desirable to provide a similar flow of air across an exterior surface of the lens 22, the nozzle 26 is provided with a through-extending slot 32 on an exterior surface thereof whereby some of the air passing through the conduit 14 will be directed across an exterior surface of the lens. This further slot 32 is also concavely shaped so as to direct a greater flow of air across a mid portion of a lens 22 and is also designed to have such flow of air strike a mid portion of the lens so as to allow it to be directed outwardly across the exterior lens surface. Desirably, an equal flow of air will then be directed across both interior and exterior surfaces of the lens 22 at any given moment.

Figure 2:
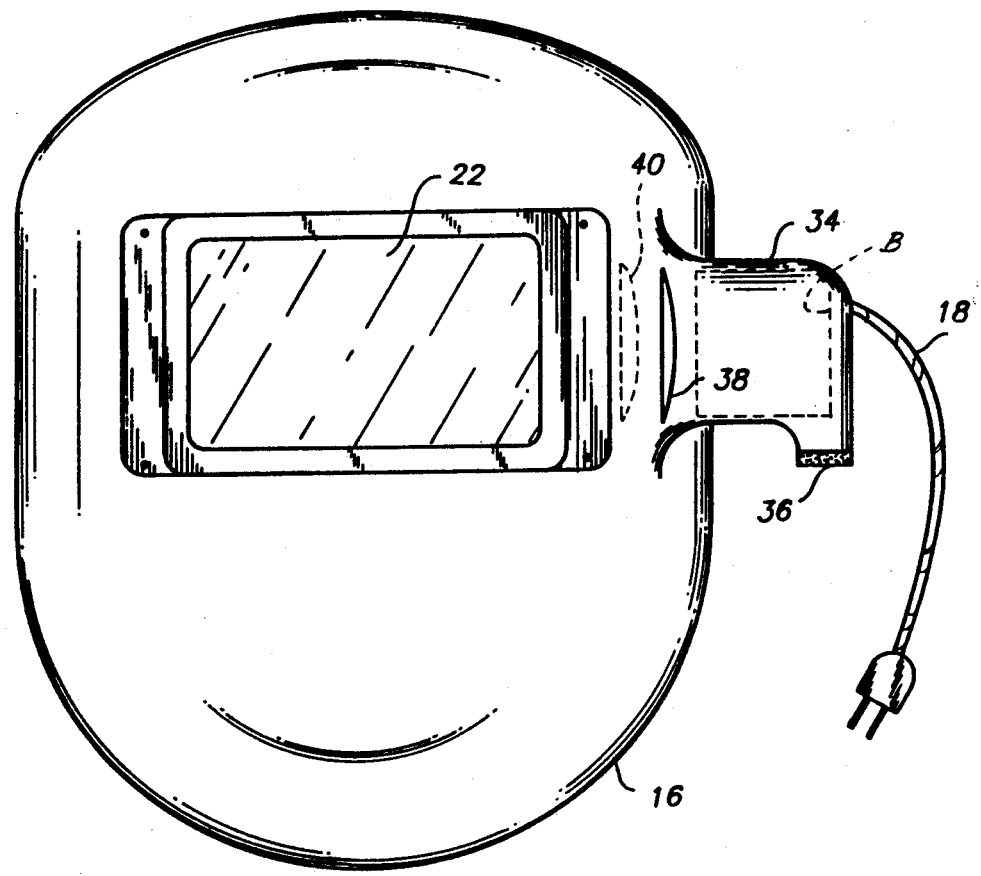
FIG. 2 is a front elevation view of a second embodiment of the invention.

FIG. 2 of the drawings illustrates the welding face shield 16 in a modified form wherein a blower unit containing a conventional blower means "B" is located within a manifold 34 (i.e. a connection means) integrally attached to a side portion of the shield. In this modified embodiment, either an external power supply, as represented by the electrical conductor 18, or an interior battery power supply can be utilized. As with the first embodiment of the invention, the air intake is covered by an appropriate charcoal filter 36. An unillustrated interiorly positioned air flow slot 40 (i.e. a first nozzle) directs air across an interior surface of the lens 22 while an exterior concavely shaped air flow slot 38 (i.e. a second nozzle) directs a similar flow of air across an exterior surface of the lens. As can be appreciated, both embodiments of the invention 10 provide filtered air to the welder for breathing, while also preventing dust accumulation on an exterior lens surface and condensation from the welder's breath on an interior lens surface.

As to the manner of usage and operation of the present invention, the same should be apparent from the above description. Accordingly, no further discussion relative to the manner of usage and operation will be provided.

With respect to the, above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters patent of the United States is as follows:

1. A new and improved ventilated welding helmet construction comprising:

a welding face shield having an elongate light filtering viewing lens mounted on a forward wall of the welding shield, said forward wall integrally mounted to first and second side walls, blower means integrally mounted on said second side wall for generating a flow to direct ventilating air only longitudinally of said elongate viewing lens;

a power supply means for operating said blower means;

connection means for directing said flow of air from said blower means to said welding face shield; and air directing means for directing said flow of air longitudinally only across interior and exterior surfaces of said viewing lens, and wherein said air directing means includes first and second nozzles forming a part of said connections means, and wherein said first nozzle directs said flow of air across said interior surface of said viewing lens and said second nozzle directs said flow of air across said exterior surface of said viewing lens, and wherein said connection means comprises an integral manifold attached to the second side of said welding face shield adjacent said viewing lens, said blower means being retained within said manifold.

* * * * *